United States Patent [19]

Lankau et al.

[11] Patent Number: 6,071,911
[45] Date of Patent: *Jun. 6, 2000

[54] 4-AMINO-1-ARYLPYRIDIN-2-ONES AND PROCESS FOR MAKING

[75] Inventors: Hans-Joachim Lankau, Weinböhla; Klaus Unverferth, Dresden; Thomas Arnold, Radebeul; Reni Bartsch; Abgelika Rostock, both of Dresden, all of Germany; Vladimir Granik; Sofia Grizik, both of Moscow, Russian Federation

[73] Assignee: Arzneimittelwerk Dresden GmbH, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 09/370,640

[22] Filed: Aug. 6, 1999

[30] Foreign Application Priority Data

Aug. 7, 1998 [DE] Germany ............... 198 35 918

[51] Int. Cl.⁷ .................................. A61K 31/535
[52] U.S. Cl. .................. 514/235.5; 514/349; 544/131; 546/297
[58] Field of Search ............ 544/131; 546/297; 514/235.5

[56] References Cited

FOREIGN PATENT DOCUMENTS 51-118768  10/1976  Japan .

OTHER PUBLICATIONS

Senda, et al, *Chemical Abstracts*, vol. 86, No. 189720, 1977.

*Primary Examiner*—Robert W. Ramsuer
*Attorney, Agent, or Firm*—Schweitzer Cornman Gross & Bondell LLP

[57] ABSTRACT

Antiepileptic compounds of the formula

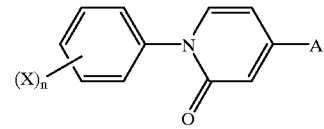

(1)

wherein X is hydrogen, a $C_{1-4}$ alkyl, $C_{1-4}$ alkoxy, trifluoromethyl, trifluoromethoxy or halogen residue, A is an amino, $C_{1-4}$ alkylamino, $C_{1-4}$ dialkylamino, morpholino, piperidino or pyrrolidino residue, and n is a cardinal number from 0 to 5, and process for preparing the foregoing compounds and for their use as anticonvulsives.

17 Claims, No Drawings

4-AMINO-1-ARYLPYRIDIN-2-ONES AND PROCESS FOR MAKING

FIELD OF INVENTION

The invention relates to novel 4-amino-1-arylpyridin-2-ones, processes for their preparation, and for their use for the treatment of various forms of epilepsy.

BACKGROUND

4-Aminopyridin-2-ones unsubstituted in the 1-position are obtained, according to the prior art, by reaction of 4-hydroxy-1H-pyridin-2-ones with amine derivatives [Synthesis; 9 (1984); 765–766)]. A further arylation in the 1-position to give compounds of formula (1) is not possible, so that the compounds according to the invention cannot be prepared according to this process.

Another process describes the synthesis of 1-aryl-4-amino-3-cyano-5-alkoxycarbonylpyridin-2-ones [Chem. Ber. 114(11); (1981); 3471–3484]. Since dimeric cyanoacetic acid esters are used as starting materials in this process, substituents are necessary in the 3- and 5-positions on the pyridin-2-one, so that the compounds according to the invention can likewise not be obtained according to this process.

A large number of compounds having anticonvulsive activity are known. However, there is a still a great need for new anticonvulsives, since even today still not all epileptic disorders can be satisfactorily treated.

DESCRIPTION OF THE INVENTION

The object of the present invention is to provide novel compounds having favorable pharmacological properties, which can be employed as antiepileptics.

According to the present invention, these novel compounds are 4-amino-1-arylpyridin-2-ones of formula (1)

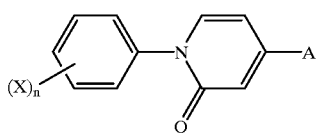

in which
X is hydrogen, a $C_{1-4}$ alkyl, $C_{1-4}$ alkoxy, trifluoromethyl, trifluoromethoxy or a halogen residue,
A is an amino, $C_{1-4}$ alkylamino, $C_{1-4}$ dialkylamino, morpholino, piperidino or pyrrolidino residue, and
n is a cardinal number from 0 to 5.

4-Amino-1-arylpyridin-2-ones of formula (1) have not been previously described.

Examples of compounds of formula (1) include;
4-amino-1-phenylpyridin-2-one;
4-amino-1-(2-chlorophenyl)pyridin-2-one;
4-amino-1-(4-chlorophenyl)pyridin-2-one;
4-amino-1-(2-methylphenyl)pyridin-2-one;
4-amino-1-(3-methylphenyl)pyridin-2-one;
4-amino-1-(4-methylphenyl)pyridin-2-one;
4-amino-1-(4-methoxyphenyl)pyridin-2-one;
4-amino-1-(4-trifluoromethoxyphenyl)pyridin-2-one;
4-amino-1-(2,6-dichlorophenyl)pyridin-2-one;
4-amino-1-(2-fluorophenyl)pyridin-2-one;
4-amino-1-(4-fluorophenyl)pyridin-2-one;
4-amino-1-(2,6-difluorophenyl)pyridin-2-one;
4-amino-1-(2-chloro-4-fluorophenyl)pyridin-2-one;
1-(2-chlorophenyl)-4-dimethylaminopyridin-2-one; and
1-(2-chlorophenyl)-4-(4-morpholino)pyridin-2-one;

According to the present invention compounds of formula (1) can be prepared by heating a compound of formula (2)

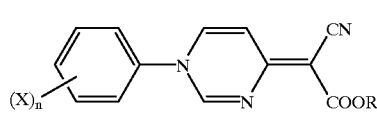

in which
X is hydrogen, a $C_{1-4}$ alkyl, $C_{1-4}$ alkoxy, trifluoromethyl, trifluoromethoxy or halogen residue,
R is a $C_{1-4}$ alkyl residue, and
n is a cardinal number from 0 to 5
in an alkaline medium at a lower temperature, and then in a strongly acidic medium at a higher temperature.

Pyrimidine derivatives of formula (2) can be synthesized in a simple, known manner, such as described in Chem. Heterocycl. Compd. 24(8), (1988), pp. 914–919; Khim. Geterotsikl. Soedin. 8 (1988), pp. 1109–1114.

The compounds of formula (1) are prepared in two process stages, wherein pyrimidine derivatives of formula (2) are heated at from about 50° C. to about 150° C. in an alkaline medium, suitably in a from about 5% wt. to about 50% wt. sodium hydroxide solution, for from about 0.1 to about 10 hours, suitably about one hour. The mixture is then heated at from about 100° C. to about 200° C. with a strong acid, suitably a from about 50% wt. to about 98% wt. sulfuric acid solution, for from about 10 to about 30 minutes. The primary amino group can be mono- or dialkylated in a manner known per se. Suitably alkylation is carried out by suitably using dimethyl sulfate, methyl iodide, 1,4-dibromobutane, 1,5-dibromopentane, or di(2-chloroethyl) ether.

The compounds of formula (1) of the present invention can bee used for preparing pharmaceutical compositions containing at least one of the compounds of formula (1) as the pharmaceutically active ingredient. Conventional pharmaceutical excipients and auxiliaries can be used for the production of the pharmaceutical compositions.

The drugs based on the compounds of formula (1) can be administered, for example, parenterally such as intravenously, intramuscularly, subcutaneously, or orally. Appropriate forms of administration can be prepared according to conventional processes that are customary in pharmaceutical practice.

The compounds of the present invention have strong anticonvulsive activity. The compounds were tested for their anticonvulsive action in vivo after i.p. administration to mice, or after (p.o. administration) to rats according to the internationally customary standard (Pharmac. Weekblad. Sc.Ed. 14, 132 (1992) and Antiepileptic Drugs, Third Ed., Raven Press, New York 1989).

For example, for the compound 4-amino-1-phenylpyridin-2-one of Example 1 in the rat, the $ED_{50}$ (p.o.) was determined to be 3.1 mg/kg for the maximal electroshock and the $ED_{50}$=200 mg/kg for the rotorod. In comparison with this, known antiepileptics either only react at relatively high doses in the maximal electroshock model or have relatively strong, undesired (neurotoxic) side effects. The following examples of Table 1 illustrate the effects obtainable with various compounds of formula (1), and the comparison of the effect to some controls.

TABLE 1

| Example | X | A | Test[1] | Dose[2] | Action[3] |
|---|---|---|---|---|---|
| 1 | H | NH$_2$ | MES | 10 | 30 |
|  |  |  | Rotorod | 100 | 40 |
| 2 | 4-Cl | NH$_2$ | MES | 100 | 30 |
|  |  |  | Rotorod | 300 | 0 |
| 3 | 4-CH$_3$ | NH$_2$ | MES | 30 | 100 |
|  |  |  | Rotorod | 30 | 0 |
| 4 | 2-CH$_3$ | NH$_2$ | MES | 30 | 70 |
|  |  |  | Rotorod | 100 | 0 |
| 5 | 4-CH$_3$—O | NH$_2$ | MES | 30 | 30 |
|  |  |  | Rotorod | 300 | 0 |
| 6 | 4-CF$_3$—O | NH$_2$ | MES | 100 | 70 |
|  |  |  | Rotorod | 300 | 0 |
| 7 | 3-CH$_3$ | NH$_2$ | MES | 30 | 100 |
|  |  |  | Rotorod | 30 | 0 |
| 8 | 3-Cl | NH$_2$ | MES | 100 | 50 |
|  |  |  | Rotorod | 100 | 15 |
| 9 | 2-Cl, 6-Cl | NH$_2$ | MES | 100 | 70 |
|  |  |  | Rotorod | 300 | 0 |
| 10 | 4-F | NH$_2$ | MES | 10 | 30 |
|  |  |  | Rotorod | 100 | 0 |
| 11 | 2-Cl, 3-Cl | NH$_2$ | MES | 30 | 30 |
|  |  |  | Rotorod | 100 | 30 |
| 12 | 2-F | NH$_2$ | MES | 30 | 100 |
|  |  |  | Rotorod | 100 | 15 |
| 13 | 2-Cl | NH$_2$ | MES | 10 | 70 |
|  |  |  | Rotorod | 30 | 15 |
| 14 | 2-F, 6-F | NH$_2$ | MES | 30 | 100 |
|  |  |  | Rotorod | 30 | 0 |
| 15 | 2-Cl, 4-F | NH$_2$ | MES | 10 | 100 |
|  |  |  | Rotorod | 100 | 30 |
| 16 | 2-Cl | N(CH$_3$)$_2$ | MES | 30 | 30 |
|  |  |  | Rotorod | 30 | 0 |
| 17 | 2-Cl | N(CH$_2$CH$_2$)O | MES | 30 | 100 |
|  |  |  | Rotorod | 30 | 0 |
| Controls |  |  |  |  |  |
| Carbamazepine |  |  | MES | 100 | 100 |
|  |  |  | Rotorod | 100 | 60 |
| Valproate |  |  | MES | 100 | 10 |
|  |  |  | Rotorod | 100 | 0 |

Footnotes to Table 1:
[1]Mouse i.p.:
MES = maximal electroshock
Rotorod = neurotoxicity
[2]in mg/kg
[3]in % of the protected animals or % animals having a visible neurotoxic action The anticonvulsive activity found and the low side effect potential of the claimed compounds enable the preparation and use of novel medicaments for the treatment of epilepsies of various forms.

The following examples of Table 2 illustrate the preparation of the compounds according to the invention.

The compounds of examples 18–32 used in the following synthesis examples were prepared in the following manner. 0.05 mol of pyrimidine derivative of formula (2) is heated under reflux for one hour in 100 ml of 10 per cent sodium hydroxide solution. After cooling, the reaction mixture is filtered and the filter residue is washed twice with 50 ml of water each time. The solid is treated with 100 ml of 75 per cent sulfuric acid and heated to 180° C. in a preheated oil bath. After a few minutes ( the reaction time shown in Table 2), the reaction mixture is rapidly cooled, diluted with 200 ml of water and rendered alkaline using ammonia solution. The precipitate is separated off and recrystallized.

The compounds of the following Examples 33–34 were prepared by alkylating a 4-aminopyridin-2-one of Examples 18–32 with an alkylating agent such as dimethyl sulfate or di(2-chloroethyl) ether in the presence of sodium methoxide. The reaction mixture is introduced into water, the precipitate is separated off and recrystallized.

TABLE 2

| Example | X | A | time | Recrystal. fr. | m.p. (° C.) | Yield (%) |
|---|---|---|---|---|---|---|
| 18 | H | NH$_2$ | 15 | ethanol | 288 | 67 |
| 19 | 4-Cl | NH$_2$ | 15 | methanol | 312 | 71 |
| 20 | 4-CH$_3$ | NH$_2$ | 15 | ethanol | 283 | 38 |
| 21 | 2-CH$_3$ | NH$_2$ | 30 | methanol | 267 | 31 |
| 22 | 4-CH$_3$—O | NH$_2$ | 15 | isopropanol | 298 | 21 |
| 23 | 4-CF$_3$—O | NH$_2$ | 10 | methanol | 296 | 44 |
| 24 | 3-CH$_3$ | NH$_2$ | 20 | isopropanol | 243 | 40 |
| 25 | 3-Cl | NH$_2$ | 15 | methanol | 285 | 62 |
| 25 | 2-Cl, 6-Cl | NH$_2$ | 20 | isopropanol | 282 | 46 |
| 27 | 4-F | NH$_2$ | 15 | isopropanol | 283 | 58 |
| 28 | 2-Cl, 3-Cl | NH$_2$ | 11 | isopropanol | 270 | 32 |
| 29 | 2-F | NH$_2$ | 15 | ethanol | 270 | 55 |
| 30 | 2-Cl | NH$_2$ | 15 | ethanol | 259 | 64 |
| 31 | 2-F, 6-F | NH$_2$ | 15 | isopropanol | 216 | 51 |
| 32 | 2-Cl, 4-F | NH$_2$ | 20 | isopropanol | 255 | 66 |
| 33 | 2-Cl | N(CH$_3$)$_2$ | 15 | isopropanol | 185 | 68 |
| 34 | 2-Cl | N(CH$_2$CH$_2$)O | 15 | isopropanol | 183 | 52 |

We claim:

1. A compound of formula (1)

$$(X)_n\text{—}C_6H_4\text{—N(pyridin-2-one)-A} \tag{1}$$

wherein

X is hydrogen, a $C_{1-4}$ alkyl, $C_{1-4}$ alkoxy, trifluoromethyl, trifluoromethoxy or halogen residue, A is an amino, morpholino, piperidino or pyrrolidino residue, and n is a cardinal number from 0 to 5.

2. A compound of claim 1, which is:

4-amino-1-phenylpyridin-2-one;

4-amino-1-(2-chlorophenyl)pyridin-2-one;

4-amino-1-(4-chlorophenyl)pyridin-2-one;

4-amino-1-(2-methylphenyl)pyridin-2-one;

4-amino-1-(3-methylphenyl)pyridin-2-one;

4-amino-1-(4-methylphenyl)pyridin-2-one;

4-amino-1-(4-methoxyphenyl)pyridin-2-one;

4-amino-1-(4-trifluoromethoxyphenyl)pyridin-2-one;

4-amino-1-(2,6-dichlorophenyl)pyridin-2-one;

4-amino-1-(2-fluorophenyl)pyridin-2-one;

4-amino-1-(4-fluorophenyl)pyridin-2-one;

4-amino-1-(2,6-difluorophenyl)pyridin-2-one;

4-amino-1-(2-chloro-4-fluorophenyl)pyridin-2-one;

1-(2-chlorophenyl)-4-(4-morpholino)pyridin-2-one.

3. A process for preparing a compound of claim 1, which comprises heating at a lower temperature in an alkaline medium, and then heating at a higher temperature in a strongly acidic medium a compound of formula (2)

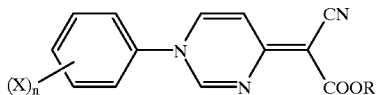

wherein

X is hydrogen, a $C_{1-4}$ alkyl, $C_{1-4}$ alkoxy, trifluoromethyl, trifluoromethoxy or halogen residue, R is a $C_{1-4}$ alkyl residue, and n is a cardinal number from 0 to 5.

4. The process of claim 3, wherein said lower temperature is from about 50° C. to about 150° C.

5. The process of claim 3, wherein said higher temperature is from about 100° C. to about 200° C.

6. The process of claim 4, wherein said heating at said lower temperature is for a period of from about 0.1 to about 10 hours.

7. The process of claim 5, wherein said heating at said higher temperature is for a period of from about 10 minutes to about 30 minutes.

8. The process of claim 3, wherein said heating at said lower temperature is from about 50° C. to about 150° C. for a period of from about 0.1 to about 10 hours, and said heating at a higher temperature is from about 100° C. to about 200° C. for a period of from about 10 minutes to about 30 minutes.

9. The process of claim 3, wherein said alkaline medium is a from about 5% wt. to about 50% wt. NaOH solution.

10. The process of claim 4, wherein said heating at said lower temperature is for a period of for about 1 hour.

11. The process of claim 5, wherein said heating at a higher temperature is carried out in a from about 50% wt. to about 98% wt. sulfuric acid solution.

12. The process of claim 8, further comprising after said heating at said higher temperature alkylating the material in an alkaline medium.

13. The process of claim 12, wherein said alkylating is carried out with at least one of dimethyl sulfate, methyl iodide, 1,4-dibromobutane, 1,5-dibromopentane, and di(2-chloroethyl) ether.

14. An antiepileptic composition containing as its active ingredient an antiepileptically effective amount of a compound of claim 1.

15. An antiepileptic composition containing as its active ingredient an antiepileptically effective amount of a compound of claim 2.

16. A process for treating a patient in need therefor with the composition of claim 14.

17. A process for treating a patient in need therefor with the composition of claim 15.

* * * * *